(12) United States Patent
Barnes et al.

(10) Patent No.: US 10,342,921 B2
(45) Date of Patent: Jul. 9, 2019

(54) INTEGRATED INFUSION PUMP AND CONTAINER

(71) Applicant: CareFusion 303, Inc., San Diego, CA (US)

(72) Inventors: Erik Barnes, Solana Beach, CA (US); Robert Dwaine Butterfield, Poway, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 15/413,321

(22) Filed: Jan. 23, 2017

(65) Prior Publication Data

US 2017/0128669 A1 May 11, 2017

Related U.S. Application Data

(63) Continuation of application No. 12/986,071, filed on Jan. 6, 2011, now Pat. No. 9,561,322.

(51) Int. Cl.
*A61M 5/14* (2006.01)
*A61M 5/36* (2006.01)
(Continued)

(52) U.S. Cl.
CPC ............ *A61M 5/172* (2013.01); *A61M 5/142* (2013.01); *A61M 5/1413* (2013.01); *A61M 5/16854* (2013.01); *A61M 5/365* (2013.01); *A61M 39/10* (2013.01); *G06F 19/3468* (2013.01); *A61M 5/14228* (2013.01); *A61M 5/14232* (2013.01);
(Continued)

(58) Field of Classification Search
CPC ...... A61M 5/172; A61M 39/10; A61M 5/365; A61M 5/16854; A61M 5/1413; A61M 5/142; A61M 2205/3584; A61M 2205/6072; A61M 2205/6063; A61M 2205/6054; A61M 2205/3553; A61M 2205/3569; A61M 2205/123; A61M 2005/16863; A61M 2205/14; A61M 2209/086; A61M 2205/502;
(Continued)

(56) References Cited

U.S. PATENT DOCUMENTS 5,399,166 A  3/1995  Laing
5,699,091 A  12/1997  Bullock et al.
(Continued)

FOREIGN PATENT DOCUMENTS

DE  102007055636 A1  5/2009
EP  0354324 A2  2/1990
EP  1985322 A1  10/2008

OTHER PUBLICATIONS

Extended European Search Report for Aplication No. 11855049.0, dated Jun. 16, 2014, 7 pages.
(Continued)

*Primary Examiner* — Lauren P Farrar
(74) *Attorney, Agent, or Firm* — Morgan, Lewis & Bockius LLP

(57) ABSTRACT

An integrated pump module is disclosed that includes a rigid housing having a fluid outlet, a fluid reservoir within the housing, and a pumping segment coupled between the fluid reservoir and the fluid outlet. The pumping segment is configured to cause fluid to flow from the fluid reservoir to the fluid outlet.

19 Claims, 8 Drawing Sheets

(51) Int. Cl.
*A61M 39/10* (2006.01)
*A61M 5/142* (2006.01)
*A61M 5/168* (2006.01)
*A61M 5/172* (2006.01)
*G06F 19/00* (2018.01)

(52) U.S. Cl.
CPC .............. *A61M 2005/16863* (2013.01); *A61M 2205/123* (2013.01); *A61M 2205/14* (2013.01); *A61M 2205/3553* (2013.01); *A61M 2205/3569* (2013.01); *A61M 2205/3584* (2013.01); *A61M 2205/50* (2013.01); *A61M 2205/502* (2013.01); *A61M 2205/52* (2013.01); *A61M 2205/6009* (2013.01); *A61M 2205/6054* (2013.01); *A61M 2205/6063* (2013.01); *A61M 2205/6072* (2013.01); *A61M 2209/045* (2013.01); *A61M 2209/086* (2013.01)

(58) Field of Classification Search
CPC .......... A61M 2205/50; A61M 2205/52; A61M 2205/6009; G06F 19/3468
See application file for complete search history.

(56) References Cited

U.S. PATENT DOCUMENTS

| | | | |
|---|---|---|---|
| 5,879,329 A | 3/1999 | Ginsburg | |
| 6,019,449 A | 2/2000 | Bullock et al. | |
| 6,065,824 A | 5/2000 | Bullock et al. | |
| 2004/0064097 A1 | 4/2004 | Peterson | |
| 2006/0031099 A1 | 2/2006 | Vitello et al. | |
| 2006/0042631 A1 | 3/2006 | Martin et al. | |
| 2006/0042632 A1 | 3/2006 | Bishop et al. | |
| 2006/0042633 A1* | 3/2006 | Bishop | A61B 5/0836 128/207.18 |
| 2007/0135765 A1 | 6/2007 | Miller et al. | |
| 2007/0191789 A1 | 8/2007 | Hickle | |
| 2007/0255260 A1* | 11/2007 | Haase | A61M 5/14276 604/891.1 |
| 2008/0015493 A1 | 1/2008 | Childers et al. | |
| 2008/0275422 A1 | 11/2008 | Ross | |
| 2009/0177991 A1 | 7/2009 | Davis et al. | |
| 2010/0037680 A1 | 2/2010 | Moberg et al. | |
| 2011/0152756 A1 | 6/2011 | Drew | |
| 2011/0152770 A1* | 6/2011 | DiPerna | A61M 5/1413 604/151 |
| 2011/0190702 A1 | 8/2011 | Stumber | |
| 2011/0282300 A1 | 11/2011 | Kriesel et al. | |

OTHER PUBLICATIONS

International Preliminary Report on Patentabilitiy for Application No. PCT/US2011/068223, dated Jul. 10, 2013, 7 pages.
International Search Report and Written Opinion for Application No. PCT/US2011/068223, dated Aug. 14, 2012, 11 pages.
European Communication under Rule 71(3) EPC for Application No. 17165052.6, dated Dec. 18, 2018, 47 pages.

* cited by examiner

INTEGRATED INFUSION PUMP AND CONTAINER

CROSS-REFERENCE TO RELATED APPLICATION

This Application is a continuation of U.S. patent application Ser. No. 12/986,071, filed Jan. 6, 2011, entitled "INTEGRATED INFUSION PUMP AND CONTAINER," the disclosure of which is incorporated herein by reference in its entirety for all purposes.

FIELD OF THE INVENTION

The present disclosure generally relates to systems and methods of delivering medical fluid to patients, and, in particular, relates to infusion pumps.

BACKGROUND

Infusion pumps have become commonplace within the healthcare world as a way to precisely administer intravenous (IV) fluids. Use of a pump in place of an elevated fluid container with a simple roller clamp to control the flow of the IV fluid allows more accurate and consistent control of the rate of delivery of the fluid to the patient.

The assembly of tubing, valves, fittings, and needles that connect the fluid container to the patient may be referred to as an "IV set." IV sets are typically disposable to reduce the risk of infection and contamination. When used with an infusion pump, the IV set includes a segment intended to be manipulated by the pump to cause the fluid to flow at a controlled rate. For a peristaltic type of pump, this segment may be as simple as a length of tubing that is fitted into the pumping compartment. A patient 10 receiving an infusion of medical fluid from a fluid container 14 delivered by a typical IV pump system 12 using an IV set 18 is shown in FIG. 1. A typical IV set 18 is depicted in FIG. 2 and described in more detail in a later section.

One of the challenges of the system depicted in FIG. 1 is that the IV set 18 is manually attached to the fluid container 14 and coupled to a pumping module 20 of IV pump 12 and then the pumping module 20 is programmed through the central control unit 16. It can be seen that the infusion pump 12 in FIG. 1 has three pumping modules 20A, 20B, 20C attached, and some IV pumps may have four or more pumping modules 20. There is therefore a risk that the nurse selects the incorrect pumping module 20 to program through the central control unit 16, resulting in the medical fluid being delivered at an incorrect rate.

In order to reduce the risk of an error being made in associating a medical fluid of container with a pumping module to which an IV set has been coupled, it is advantageous to provide an integrated fluid container and pumping module. The disclosed method and system disclose a secure integrated fluid container and pumping cassette for use with a compatible IV pump and a filling station for filling the integrated pump module.

An integrated pump module is disclosed that includes a rigid housing having a fluid outlet, a fluid reservoir, and a pumping segment coupled between the fluid reservoir and the fluid outlet. The pumping segment is configured to cause fluid to flow from the fluid reservoir to the fluid outlet.

A filling station is disclosed that includes a docking location configured to receive an IV pump module having a fluid reservoir and an information element. The filling station also includes a filling connection configured to fluidically couple to the fluid reservoir, at least one inlet connection configured to accept a medical fluid from a source, and a pumping segment coupled to the source of medical fluid and the filling connection. The pumping segment is configured to transfer a selected amount of fluid from the source to the fluid reservoir. The filling station also includes a programming module that is configured to associate information with the information element, wherein the information comprises at least one of the set of a drug identifier, a patient identifier, and a pumping parameter.

A method of delivering a medical fluid to a patient is disclosed, the method comprising the step of placing an integrated pump module having a fluid reservoir and a memory in a docking location of a filling station having an inlet connection and a filling connection, wherein the fluid reservoir is fluidically coupled to the filling connection when the integrated pump module is docked. The method also includes pumping a selected amount of medical fluid from a source into the fluid reservoir, removing the integrated pump module from the filling station; coupling the integrated pump module to an IV pump that is configured to accept the Integrated pump module; and activating the IV pump to deliver the medical fluid from the fluid reservoir to the patient.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The disclosed methods and system provide an integrated pump module that is used with a compatible IV pump. The integrated pump module incorporates a fluid reservoir and a pumping segment within a rigid housing, and also includes an information element that provides information, or a link to information that is stored elsewhere, that may include identification of the medication, identification of the patient for whom the medication is intended, operating parameters for the IV pump, and other data related to the contents or use of the integrated pump module.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

The methods and systems disclosed herein are presented in terms of an intravenous administration of a medication to a patient in a healthcare environment. It will be apparent to those of ordinary skill in the art that the same systems and methods may be employed to deliver fluids in other environments and for other products. Nothing in this disclosure should be interpreted, unless specifically stated as such, to limit the application of any method or system disclosed herein to any specific environment or purpose.

Figure 1:
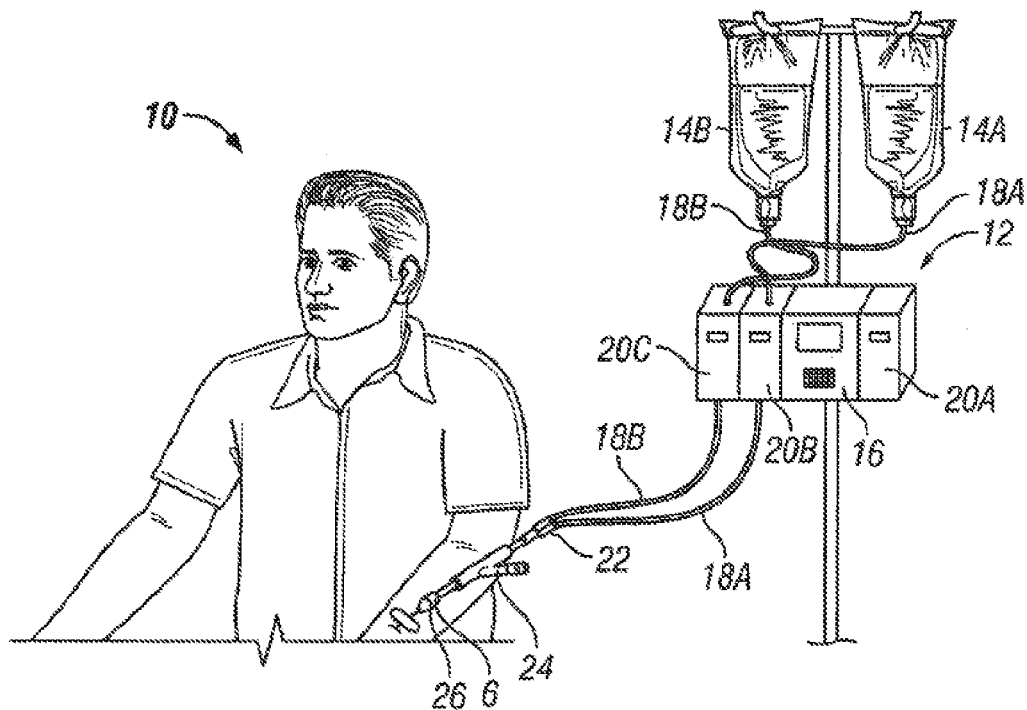
FIG. 1 depicts a patient receiving an infusion of a medical fluid using an IV pump in accordance with the prior art.

FIG. 1 depicts a patient 10 receiving an infusion of a medical fluid using an IV pump 12. In this example, the IV pump 12 includes a control module 16 and three pumping modules 20A, 20B, and 20C. In the situation depicted in FIG. 1, the patient 10 is receiving two medical fluids from containers 14A and 14B. IV set 18A is connected to container 14A and passes through pumping module 20B to connect to Y-coupling 22 which is then connected to a needleless coupling 6 that is connected to an infusion device 26 such as an IV cannula. A second IV set 18B is connected to container 14B and passes through pumping module 20C to connect to the same Y-coupling 22. It can be seen that IV set 18B loops down and around the IV pump 12 and the lines of IV sets 18A and 18B can easily be confused. It is possible that the caregiver might place IV set 18B, which is intended to pass through pumping module 20C, into pumping module 20B due the confusion of lines. If this error occurs, the medical fluid from container 14B will be administered at the rate intended for the medical fluid from container 14A.

Figure 2:
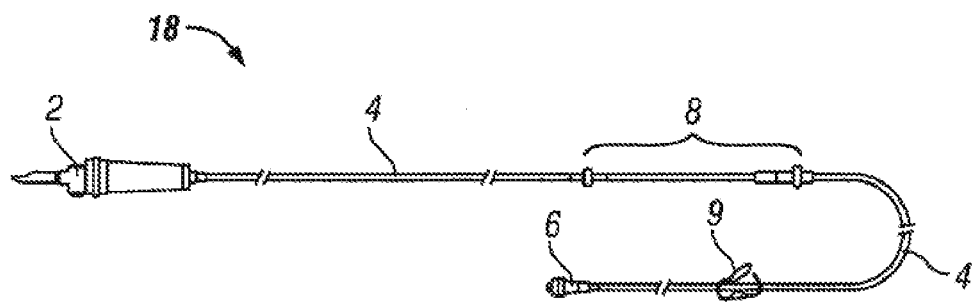
FIG. 2 depicts an example IV set in accordance with the prior art.

FIG. 2 depicts an example IV set 18. This example IV set 18 includes a bag spike 2 that is configured to connect to a fluid container such as fluid container 14 of FIG. 1. The bag spike 2 is connected through tubing 4 to a pumping segment 8 that is then connected through additional tubing 4 to a fitting 6. In this example, fitting 6 is a needleless Luer connector suitable for connection to a patient infusion device (not shown) such as an intravenous needle, as one example. Pumping segment 8 is, in this example, a section of tubing suitable for peristaltic manipulation to cause fluid to flow through the tubing and includes two alignment fittings that facilitate proper placement of the pumping segment 8 in the pumping module 20. IV set 18 also includes a clamp 9 that can be closed to stop flow through the tubing 4. In certain embodiments, the IV set includes a Y-coupling 22. In certain embodiments, the IV set includes a needleless access port 24.

Figure 3:
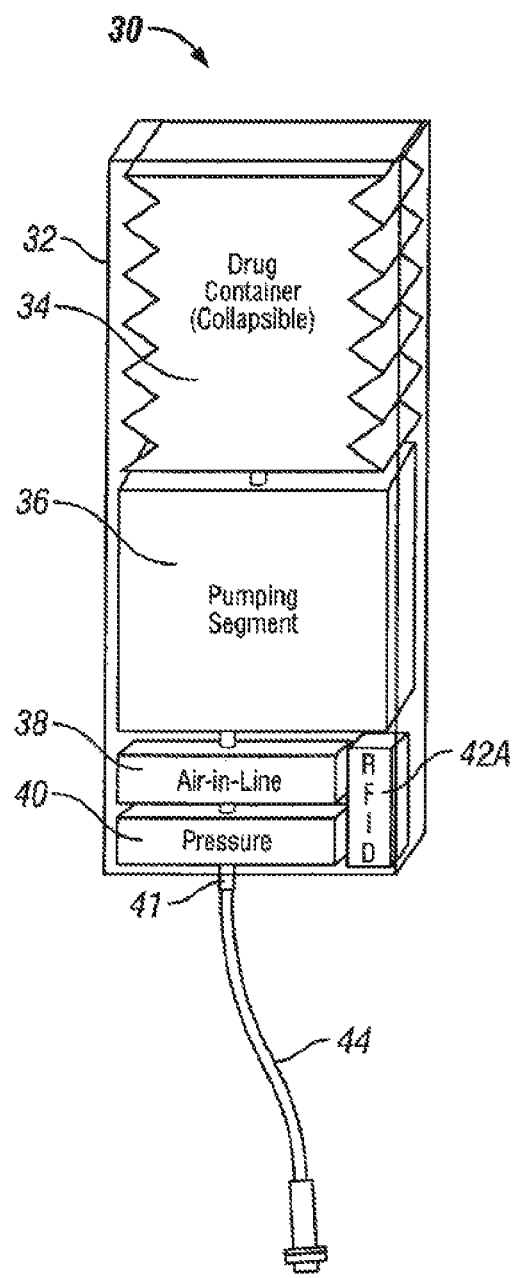
FIGS. 3-4 depict an exemplary integrated pump module according to certain aspects of this disclosure.
Figure 4:
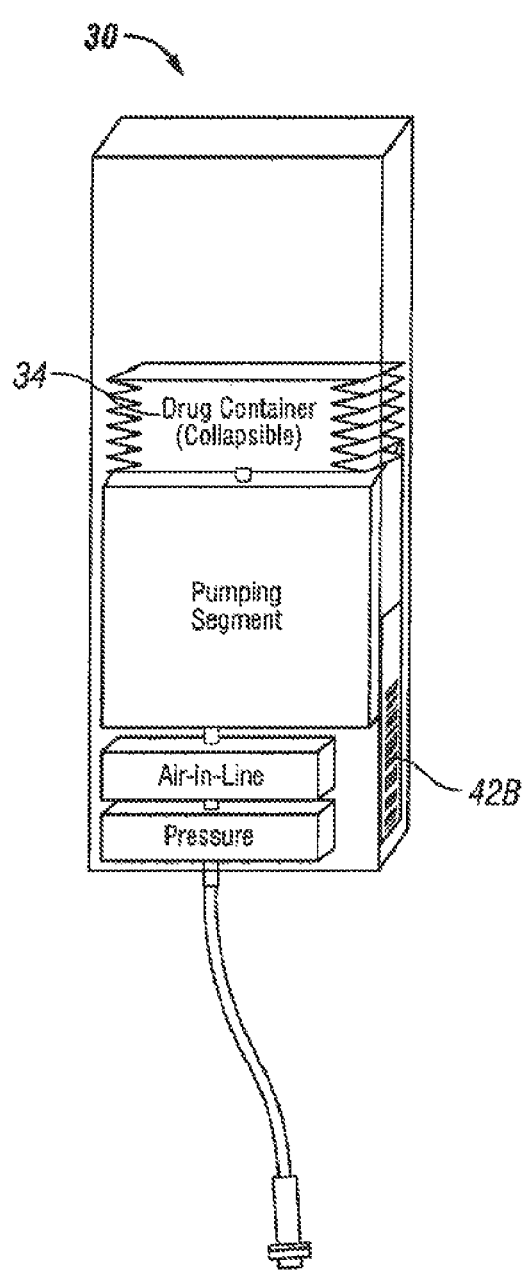
Figure 5:
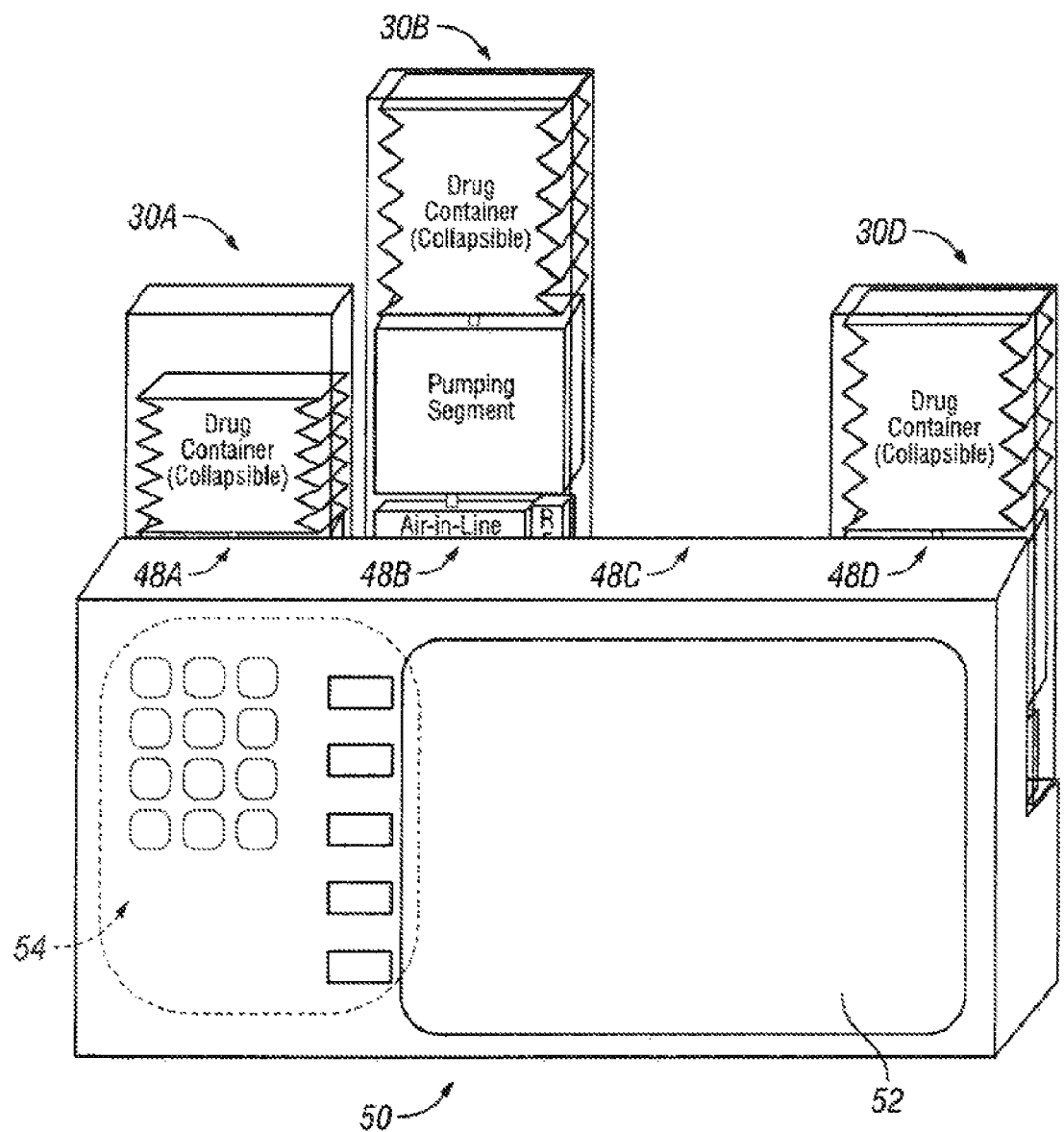
FIG. 5 depicts an exemplary IV pump configured to utilize integrated pump modules according to certain aspects of this disclosure.

FIGS. 3-4 depict an exemplary integrated pump module according to certain aspects of this disclosure. The integrated pump module 30 comprises a rigid housing 32 that contains a fluid reservoir 34 and a pumping segment 36. The fluid reservoir 34 is coupled to the pumping segment 36 and to the IV tube 44. When pumping module 30 is coupled to a compatible IV pump 50, such as shown in FIG. 5, there is no potential for an incorrect association of the fluid container 14 with the pumping module 20 of FIG. 1.

The exemplary pumping module 30 of FIG. 3 includes a Radio Frequency Identification (RFID) tag 42A that is one embodiment of an information element 42 that provides information associated with this integrated pump module 30. In the example of FIG. 3, RFID tag 42A contains a writeable memory (not shown separately) in which is stored information related to the prescription used to prepare this integrated pump module, the medication contained in the integrated pump module 30, the patient 10 for whom the medication is intended, and the operating parameters for the IV pump 50 for administration of the medication. In certain embodiments, the memory of RFID tag 42A contains other or additional information related to one or more of the integrated pump module 30, the contents of the integrated pump module 30, the patient 10, or the preparation of the integrated pump module 30, such as a lot number or expiration date of the medication. In certain embodiments, the RFID tag 42A contains only a locally unique serial number, which may be referred to as its "license plate," wherein the information listed above is stored in a database and associated with this same serial number. In these embodiments, the IV pump 50 reads the serial number from the RFID tag 42A and then accesses the database to retrieve the information stored therein that is associated with that serial number.

In certain embodiments, the information element 42 is a barcode label 42B, such as shown in FIG. 4, with a locally unique serial number, wherein this same serial number is associated with a data record in a connected database. The IV pump 50 scans the barcode label 42B, decodes the serial number, and then transmits the serial number to the database and retrieves the data record containing information about this integrated pump module 30. In certain embodiments, the information element 42 is a 2D coded matrix (not shown). In certain embodiments, the information element 42 contains enough information to eliminate the need to look up additional information in a database. In certain embodiments, information element 42 is a re-writable memory device (not shown) coupled to a connector that mates with the IV pump 50 when the integrated pump module 30 is docked with the IV pump 50. When docked, the IV pump 50 retrieves information from the memory device 42.

The exemplary pumping module 30 of FIG. 3 also includes an air-in-line sensor 38 and a pressure sensor 40. The air-in-line sensor 38 detects air bubbles in the output of pumping segment 36, thus enabling the IV pump 50 to stop pumping rather than inject the air bubbles into the bloodstream of the patient 10. With a collapsible fluid reservoir 34, however, there is no source of external air available and the air-in-line sensor 38 is omitted in certain embodiments. The pressure sensor 40 is configured to measure the pressure in IV tube 44 and thereby detect complete or partial occlusions in the IV tube 44, thus enabling the IV pump 50 to issue an alarm when an occlusion occurs.

FIG. 3 depicts a pumping module 30 with a maximum amount of medical fluid in the fluid reservoir 34, wherein it can be seen that the sides of the fluid reservoir 34 are, in this example, corrugated such that the top surface of the fluid reservoir 34 moves linearly as the volume of fluid in the fluid reservoir 34 changes. With the maximum amount of medical fluid in the fluid reservoir 34, the top of the fluid reservoir 34 is, in this example, adjacent to the top of the rigid housing 32. A pumping segment 36 is configured to couple to the pumping segment of a compatible IV pump 50 of FIG. 5 (not shown in FIG. 3), wherein the pumping segment manipulates the pumping segment 36 to cause fluid flow from the fluid reservoir 34 through outlet 41 into IV tube 44. Pumping segment 36 is similar in function to the pumping segment 8 of the IV set 18 shown in FIG. 2.

The rigid housing 32 provides secure storage of the medication that is contained in fluid reservoir 34. In certain embodiments, once the integrated pump module 30 is filled in the pharmacy, as is described later relative to FIGS. 8 and 9, the contents of the fluid reservoir 34 are not accessible except through use of the IV pump 50. This enables the use of integrated pump modules 30 to transport and administer controlled substances such as pain medications in compliance with certain federal, state, and local regulations.

FIG. 4 depicts a pumping module 30 similar to that shown in FIG. 3, wherein the information element 42 is a RFID tag 42A in FIG. 3 and a barcode label 42B in FIG. 4. In certain embodiments, the barcode label 42B is located on other surfaces of the integrated pumping module 30, such as a surface that would face the IV pump 50 when the integrated pumping module 30 is docked as shown in FIG. 5. Furthermore, FIG. 4 depicts a pumping module 30 after a portion of the fluid from the fluid reservoir 34 has been delivered to the patient 10. It can be seen that the fluid reservoir 34 has collapsed such that the top of the fluid reservoir 34 has moved from its initial position shown in FIG. 3 to a second position shown in FIG. 4. The collapsible nature of the fluid reservoir 34 provides the dual benefits of preventing air from coming into contact with the medical fluid contained in fluid reservoir 34 and providing an easily measured external indicator of the amount of fluid remaining in fluid reservoir 34. In certain embodiments, a flexible bag or elastomeric balloon is provided in place of the corrugated collapsible fluid reservoir 34.

FIG. 5 depicts an exemplary IV pump 50 configured to utilize integrated pump modules 30 according to certain aspects of this disclosure. This example IV pump 50 includes four docking stations 48, designated 48A through 48D to indicate a specific docking station, each docking station able to accept an integrated pump module 30. FIG. 5 depicts integrated pump modules 30A and 30D docked in docking stations 48A and 48D, respectively. An integrated pump module 30B is about to dock in docking station 48B, while docking station 48C is empty. This example IV pump 50 includes a display screen 52 and a data input device 56 that is, in this example, a keypad and a series of configurable buttons adjacent to display screen 52. Other types of input and output devices will be apparent to those of ordinary skill in the art without departing from the scope of the claims. In certain embodiments, the docking stations 48 are contained in a docking module (not shown) that is separate from the input and output interfaces 56 and 52. In certain embodiments, the input and output interfaces 56 and 52 are provided by a separate computer (not shown).

The integrated pump modules 30 mechanically attach to the body of IV pump 50 in the docking stations 48 with a mechanism (not shown) that both locates each integrated pump module 30 such that an electrical connection is established between the processor of the IV pump 50 and the electronics that are a part of the pumping segment of the integrated pump module 30. In certain embodiments, this mechanical attachment is accomplished with tabs (not shown) on the body of the integrated pump module 30 that slide into matching rails (not shown) on the body of the IV pump 50. In certain embodiments, the mechanical attachment is accomplished with one or more mating snap-fit features (not shown) on the integrated pump module 30 and IV pump 50. In certain embodiments, the integrated pump module 30 is held to the IV pump 50 by a magnetic element (not shown), wherein the magnetic element may be on either the integrated pump module 30 or the IV pump 50, and the other of the two may have a second magnetic element or a magnetically attracted element, such as a steel plate. Other forms of detachable coupling of components are known to those of ordinary skill in the art and may be used to attach the integrated pump module 30 to the IV pump 50.

In certain embodiments, the integrated pump modules 30 electrically connects to the IV pump 50 through a electrical connector, wherein the mating halves of the connector (not shown) are aligned and connected by the mechanical attachment provisions described above. In certain embodiments, communication between the processor of the IV pump 50 and the electronics that are a part of the pumping segment of the integrated pump module 30 is established through a wireless link (not shown). In certain embodiments, power is transferred wirelessly (not shown) between the IV pump 50 and the integrated pump module 30.

Figure 6:
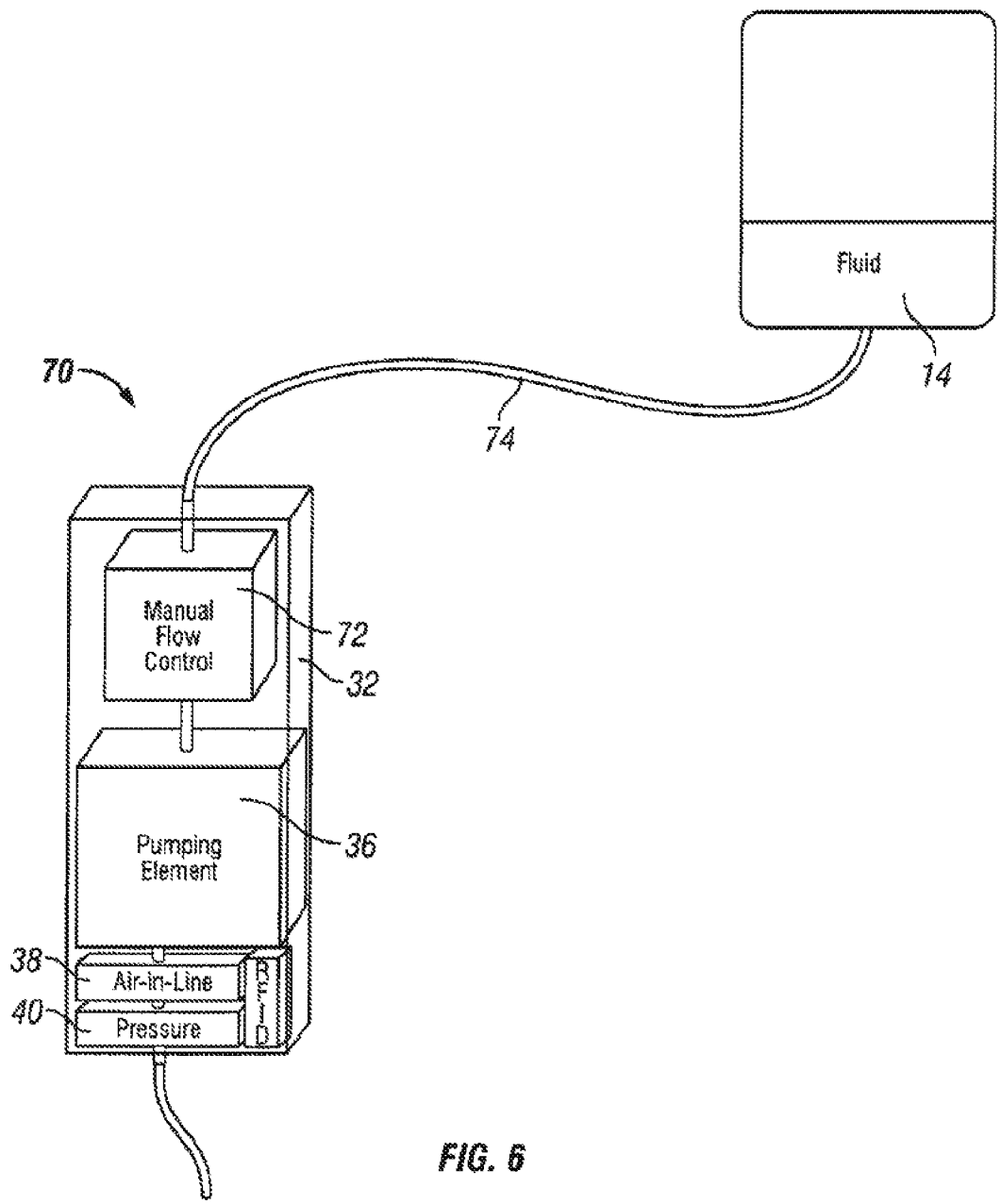
FIG. 6 depicts another embodiment of an integrated pump module according to certain aspects of this disclosure.

FIG. 6 depicts another embodiment of an integrated pump module 70 according to certain aspects of this disclosure. In this example, a fluid container 14 is permanently attached through a line 74 to a pump module 70 that includes a manual flow control 72 in place of an internal fluid reservoir 34. Pump module 70 includes the same pumping segment 36 and air-in-line sensor 38 and pressure sensor 40 as integrated pump module 30. Use of a pump module 70 in conjunction with a fluid container 14 enables the provision of a larger quantity of fluid than is possible with an internal fluid reservoir 34 in an integrated pump module 30. Attachment of the fluid container 14 to pump module 70 may be accomplished, for example, in the pharmacy and then the coupled fluid container 14 and pump module 70 transported to the patient 10. The permanent attachment of the fluid container 14 to the pump module 70 thereby creates a permanent association between the two, analogous to the embodiment of the integrated pump module 30 of FIGS. 3 and 4.

Figure 7:
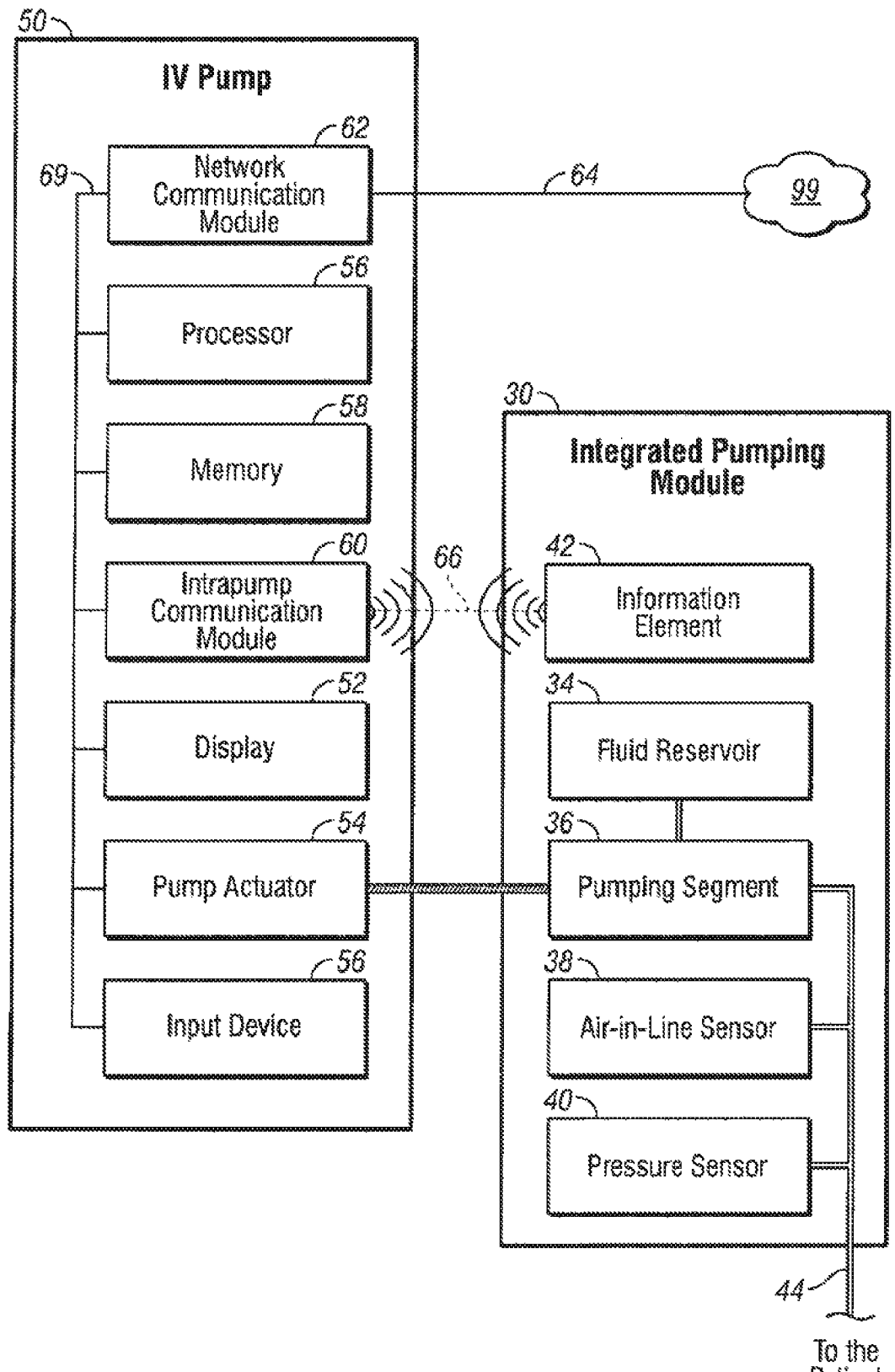
FIG. 7 is a block diagram of an IV pump and an integrated pump module according to certain aspects of this disclosure.

FIG. 7 is a block diagram of an IV pump 50 and an integrated pump module 30 according to certain aspects of this disclosure. The integrated pump module 30 is the same unit shown in FIGS. 3 and 4 and the IV pump 50 is as shown in FIG. 5. The integrated pump module 30 comprises an information element 42, a fluid reservoir 34 that is coupled to a pumping segment 36, wherein pumping segment 36 is then coupled to the IV tube 44 that would, when in use, connect to the patient 10. This exemplary integrated pump module 30 also includes an air-in-line sensor 38 and a pressure sensor 40 that are coupled to IV tube 44.

The IV pump 50 comprises a processor 56, a memory 58, an intrapump communication module 60, a display 52, a pump actuator 54, and an input device 56. The IV pump 50 also comprises a network communication module 62 that is coupled over a network 64 to an external system 99 that is presented as a "cloud." External system 99 may include one or more of Admission/Discharge/Transfer (ADT) systems, Medication Administration Record (MAR) systems, pharmacy systems, and other computerized information handling systems running on local computers, local servers, or hosted on remote computers provided by third-party service providers. In certain embodiments, network 64 includes a wireless link to a local network hub (not shown). In certain embodiments, network 64 includes a hard-wired network connection to external system 99. The processor 56 is coupled to the other elements of IV pump 50, in this example, through a network 69. In certain embodiments, one or more elements of network 69 are replaced by direct connections such as a serial RS-232 line or a direct parallel bus.

The intrapump communication module 60, in this example, comprises a RFID reader (not shown separately) that reads the RFID tags 42A of the integrated pump module 30, wherein the electromagnetic field created by the RFID reader is shown as wireless link 66. In certain embodiments, the intrapump communication module 60 comprises an optical scanner or imager (not shown separately) configured to read barcodes 42B or 2D data tags and link 66 is the optical link of the scanner to the barcode. In certain embodiments, the informational element 42 is a memory device (not shown separately) and link 66 is a hard wired connection to the memory device.

The pump actuator 54 is mechanically coupled to the pumping segment 36 of the integrated pumping module 30 when the integrated pumping module 30 is docked to the IV pump 50.

Figure 8:
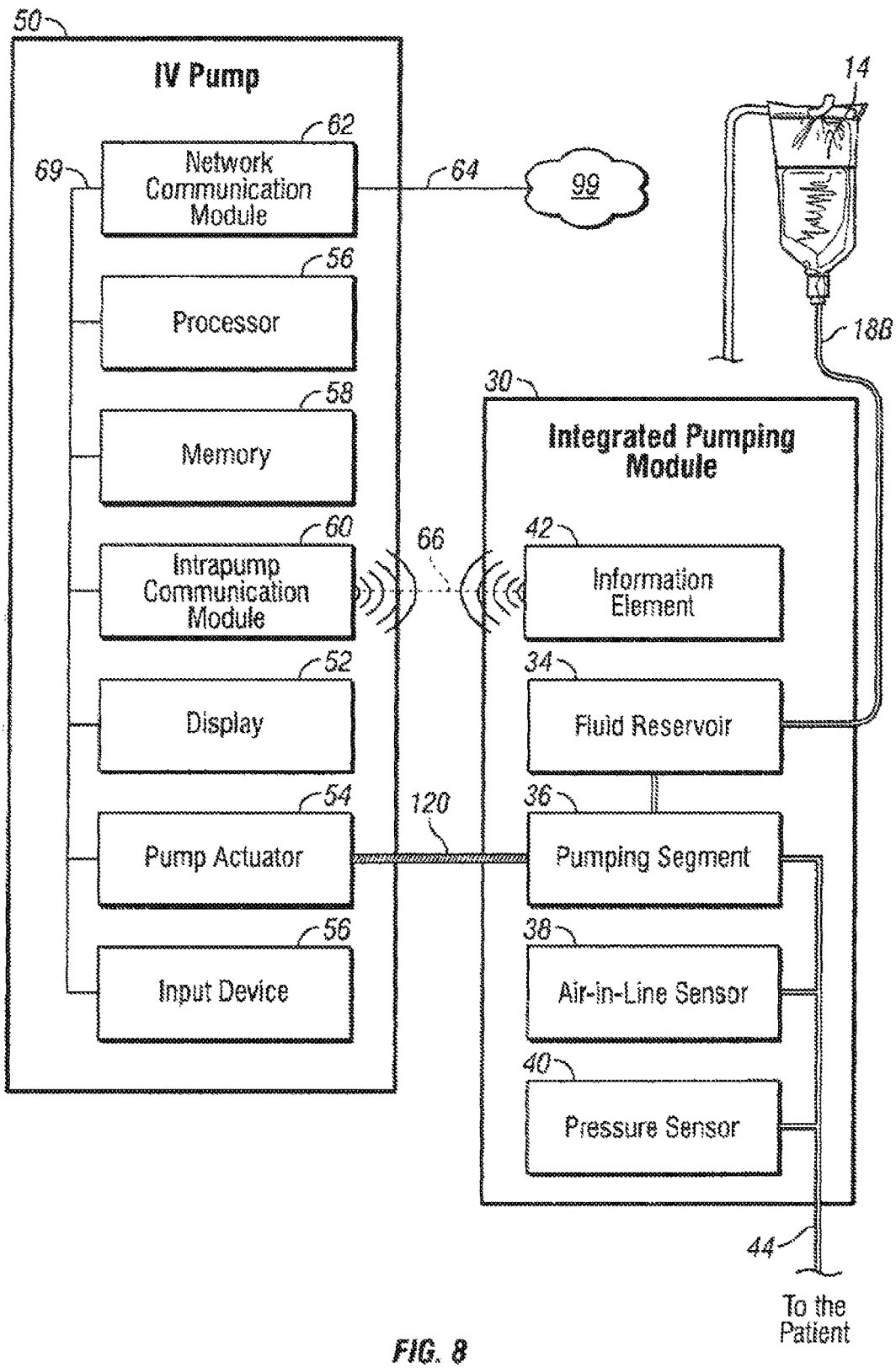
FIG. 8 is block diagram of another embodiment of an IV pump and an integrated pump module according to certain aspects of this disclosure.

FIG. 8 is block diagram of another embodiment of an IV pump 50 and an integrated pump module 30 according to certain aspects of this disclosure. In this embodiment, a container 14 of medical fluid is permanently connected to the fluid reservoir 34 through an IV set 18B. This provides a larger quantity of medical fluid while ensuring that the container 14 is associated with the correct integrated pumping module 30.

Figure 9:
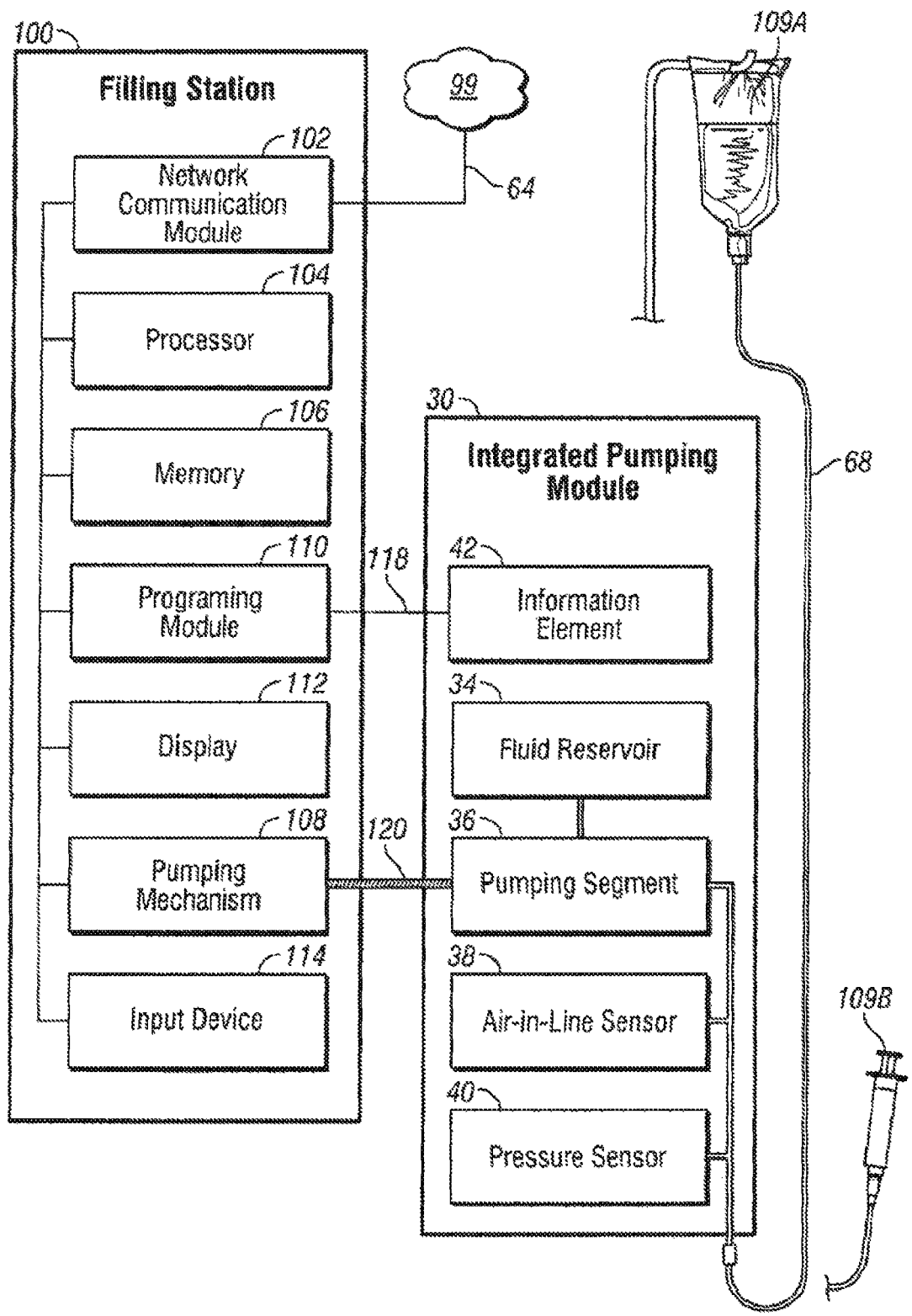
FIG. 9 is a block diagram of an exemplary filling station and an integrated pump module according to certain aspects of this disclosure.

FIG. 9 is a block diagram of an exemplary filling station 100 and an integrated pump module 30 according to certain aspects of this disclosure. The filling station 100, in this example, is located in the pharmacy of a hospital wherein prescribed medical fluids are loaded into integrated pump modules 30 that are initially empty. The external system 99 shown in FIG. 9 includes a database in which are stored prescriptions for patients in the hospital, wherein a single patient may have more than one prescription. The filling station 100 comprises a processor 104, a memory 106, a network communication module 102, a programming module 110, pumping segment 108, a display 112, and input device 114. The processor 104 downloads prescriptions through network 64 and network communication module 102 from an external system 99. Each prescription contains a specification for the amount and type of medications and medical fluids to be provided to a specific patient. When a prescription is selected to be filled, the pumping segment 36 causes the pumping segment 36, for example by running in reverse, to draw fluid from one or more sources, such as an IV bag 109A and a syringe 109B, according to the selected prescription through fill line 68 that, in this embodiment, is attached to the outlet of the pumping module 30. The programming module 110, in this example, stores information related to the prescription, such the prescription identifier, the patient, the medication or medical fluid, and an expiration date, in the information element 42. In certain embodiments, where the information element 42 is a pre-printed barcode label, the programming module 110 scans the barcode of information element 42 and then sends the information along with the decoded identification number from information element 42 through network module 102 to a database in the external system 99. In certain embodiments, integrated pump modules 30 are filled with standard medications or medical fluids that are not associated with prescriptions for specific patients.

Figure 10:
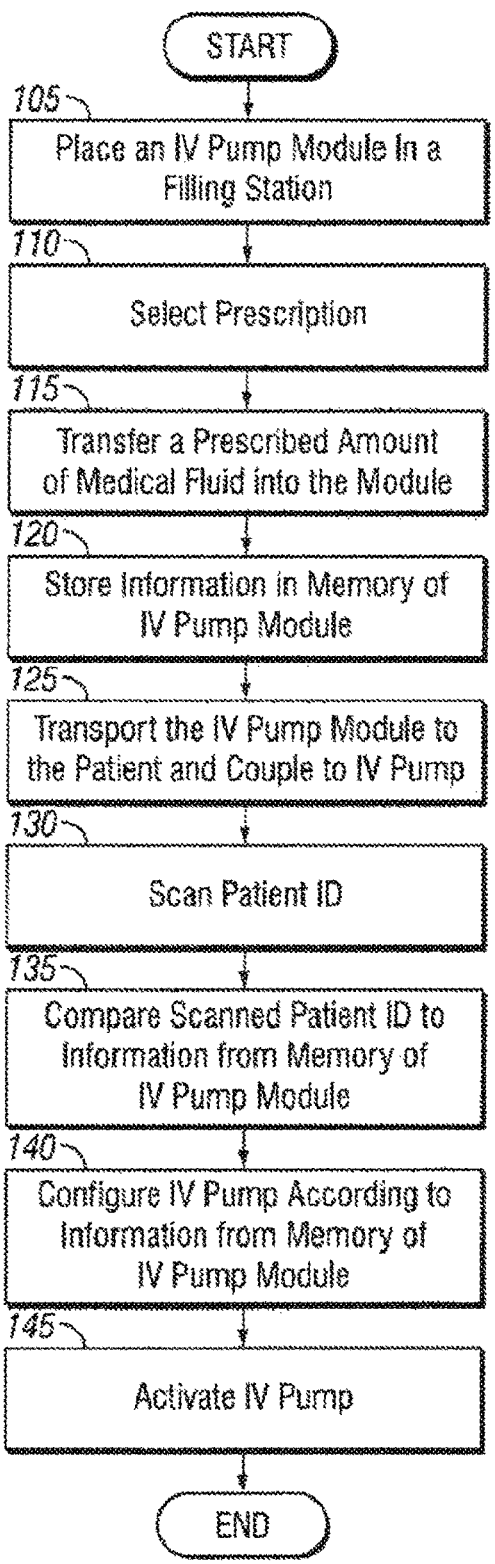
FIG. 10 is a flowchart depicting an exemplary method of delivering a medical fluid to a patient according to certain aspects of this disclosure.

FIG. 10 is a flowchart depicting an exemplary method of delivering a medical fluid to a patient 10 according to certain aspects of this disclosure. The method starts in step 105 by placing an empty integrated pump module 30 in the filling station 100 in the pharmacy. Step 110 provides for selecting the prescription to be filled. This selection may include reviewing a list of prescriptions contained in a database, selection of one of the prescriptions for filling, and then downloading the selected prescription from the database to the filling station 100. Once the prescription is downloaded, the prescribed amounts of medications and medical fluids are transferred in step 115 into the fluid reservoir 34 of the integrated pump module 30. In step 120, information associated with this prescription is stored in the information element 42 of the integrated pump module 30. In certain embodiments, the storage process consists of reading the identifier stored in the information element 42 of the integrated pump module 30 and then sending the information that is to be stored along with the decoded identification number from information element 42 through network module 102 to the database in the cloud 99. Once the fluid reservoir is filled with the prescribed amount of medication and the information is stored in the memory of the integrated pump module 30, the integrated pump module 30 is removed from the filling station in step 125 and transported to the patient where the integrated pump module 30 is coupled to an IV pump 50. In step 130, the nurse scans the patient ID, for example, from a wristband worn by the patient 10. The IV pump 50 compares this scanned patient identification to the patient identification information contained in the information element 42 of the integrated pump module 30. If the two patient identifications match, the IV pump 50 utilizes the configuration information contained in the information element 42 of the integrated pump module 30 to configure the IV pump 50 to deliver the fluid at the appropriate rate. In step 145, the nurse activates IV pump 50 and begins deliver of medical fluid to the patient 10. This delivery of fluid continues in step 145 until the end of treatment, thereby ending this method.

In summary, the disclosed method and system of providing a medical fluid to a patient includes an integrated pump module that contains both the medical fluid and the pumping segment that couples to an IV pump, thereby ensuring the correct association of the medical fluid with the pumping segment of the IV pump. The integrated pump module also includes an information element that contains information identifying one or more attributes that may include identification of the patient for whom the medication is intended, the identification of the medication in the integrated pump module, the operating parameters for the IV pump to administer the medication at the prescribed rate, or an expiration date for the medication contained in the integrated pump module. This information may be downloaded directly by the IV pump from the information element, further automating the configuration of the IV pump and ensuring that this medication is properly administered to the patient. A filling station is also disclosed such that the integrated pump modules may be filled in the pharmacy with one or more medications according to standard treatment protocols or patient specific prescriptions and then transported to the patient.

The previous description is provided to enable a person of ordinary skill in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. An integrated pump module comprising:
  a rigid housing having a top, a bottom, and a fluid outlet;
  a fluid reservoir, within the housing, comprising a top, a bottom, and sidewalls; and
  a pumping segment coupled between the fluid reservoir and the fluid outlet, the pumping segment configured to transfer fluid from the fluid outlet to the fluid reservoir and transfer fluid from the fluid reservoir to the fluid outlet, wherein the top of the fluid reservoir moves toward the housing top when fluid is transferred to the fluid reservoir, and the top of the fluid reservoir moves away from the housing top when fluid is transferred from the fluid reservoir, wherein the pumping segment is configured to be coupled to and driven by a pump actuator external to the integrated pump module.

2. The integrated pump module of claim 1, comprising an information element coupled to the housing, the information element comprising at least one of an integrated pump module identifier, a drug identifier, a patient identifier, and a pumping parameter.

3. The integrated pump module of claim 2, wherein the fluid reservoir contains a quantity of a medication and the information element comprises at least a medication identifier.

4. The integrated pump module of claim 3, wherein the information element comprises information required to administer the medication.

5. The integrated pump module of claim 2, wherein the information element comprises at least one of an optically scannable image, a writable memory, and comprises a Radio Frequency Identification (RFID) tag.

6. The integrated pump module of claim 1, wherein collapsible sidewalls prevent entry of air into the fluid reservoir as fluid is transferred to or from the fluid reservoir.

7. The integrated pump module of claim 1, comprising a sensor configured to detect a position of the fluid reservoir top as the fluid reservoir moves relative to the housing.

8. The integrated pump module of claim 7, wherein the top of the fluid reservoir comprises a first position adjacent the housing top, associated with having a maximum amount of fluid in fluid reservoir, and a second position separated from the housing top, associated with having a minimum amount of fluid in the fluid reservoir.

9. The integrated pump module of claim 1, comprising an air-in-line detector.

10. The integrated pump module of claim 1, comprising a pressure sensor.

11. The integrated pump module of claim 1, wherein the pumping segment is configured to be mechanically manipulated by the pump actuator.

12. A method of transferring a fluid using an integrated pump module, the method comprising:
  coupling a source of medical fluid to an integrated pump module comprising: a rigid housing having a top, a bottom, and a fluid outlet; and a fluid reservoir, within the housing, comprising a top, a bottom, and collapsible sidewalls, wherein the source of medical fluid is coupled with the outlet;
  driving a pumping segment, coupled between the fluid reservoir and the fluid outlet, to transfer medical fluid from the source, through the fluid outlet, to the fluid reservoir such that the top of the fluid reservoir moves toward the housing top when fluid is transferred to the fluid reservoir, wherein the pumping segment is configured to be coupled to and driven by a pump actuator external to the integrated pump module;
  decoupling the integrated pump module from the source of medical fluid; and
  driving the pumping segment to transfer the medical fluid from the fluid reservoir to the outlet such that the collapsible sidewalls fold and the top of the fluid reservoir moves away from the housing top when fluid is transferred from the fluid reservoir.

13. The method of claim 12, comprising detecting, using a sensor, a current position of the top of the fluid reservoir as the fluid reservoir moves relative to the housing.

14. The method of claim 13, comprising detecting a first position associated with having a maximum amount of fluid in fluid reservoir, and a second position associated with having a minimum amount of fluid contained in the fluid reservoir.

15. The method of claim 12, comprising coupling the integrated pump module to a docking location of a filling station.

16. The method of claim 12, comprising coupling the integrated pump module to an IV pump configured to drive the pumping segment.

17. The method of claim 12, wherein driving the pumping segment does not comprise a compressive force to the fluid reservoir.

18. The method of claim 12, wherein driving the pumping segment comprises mechanical manipulation of the pumping segment by a pump actuator.

19. The method of claim 12, wherein driving the pumping segment to transfer medical fluid from the source to the fluid reservoir comprises operating the pumping segment in a first direction, and driving the pumping segment to transfer the medical fluid from the fluid reservoir to the outlet, comprises operating the pumping segment in a second direction that is opposite the first direction.

\* \* \* \* \*